US005723659A

United States Patent [19]

White

[11] Patent Number: 5,723,659
[45] Date of Patent: Mar. 3, 1998

[54] PROCESS FOR THE PURIFICATION OF AROMATIC POLYCARBOXYLIC ACIDS

[75] Inventor: James F. White, Hudson, Ohio

[73] Assignee: Engelhard Corporation, Iselin, N.J.

[21] Appl. No.: 794,103

[22] Filed: Feb. 3, 1997

Related U.S. Application Data

[63] Continuation of Ser. No. 542,229, Nov. 6, 1995, which is a continuation of Ser. No. 360,855, Dec. 20, 1994, abandoned.

[51] Int. Cl.$^6$ ................................................... C07C 51/42
[52] U.S. Cl. ................................................................ 562/485

[56] References Cited

U.S. PATENT DOCUMENTS

| | | | |
|---|---|---|---|
| 2,976,253 | 3/1961 | Edwards | 252/430 |
| 3,584,039 | 6/1971 | Meyer | 260/525 |
| 3,726,915 | 4/1973 | Pohlmann | 260/525 |
| 3,981,976 | 9/1976 | Stevens | 423/580 |
| 3,993,584 | 11/1976 | Owen et al. | 252/383 |
| 4,201,872 | 5/1980 | Kimura et al. | 562/487 |
| 4,359,503 | 11/1982 | Harper-Tervet et al. | 428/367 |
| 4,405,809 | 9/1983 | Stech et al. | 562/487 |
| 4,552,744 | 11/1985 | Chuang et al. | 423/522 |
| 4,579,689 | 4/1986 | Hershman et al. | 260/502 |
| 4,791,226 | 12/1988 | Puskas | 562/487 |
| 4,892,972 | 1/1990 | Schroeder et al. | 562/487 |
| 5,122,583 | 6/1992 | Ewen et al. | 526/125 |
| 5,124,297 | 6/1992 | Arzoumanidis et al. | 502/120 |
| 5,137,996 | 8/1992 | Bailly et al. | 526/125 |
| 5,180,849 | 1/1993 | Taniguchi | 562/414 |
| 5,218,052 | 6/1993 | Cohen et al. | 525/240 |

FOREIGN PATENT DOCUMENTS 0476765A  3/1992  European Pat. Off.

*Primary Examiner*—Samuel Barts
*Attorney, Agent, or Firm*—Raymond F. Keller

[57] ABSTRACT

An improved process is disclosed for purifying impure aromatic polycarboxylic acids produced by the catalytic oxidation of polyalkylaromatic hydrocarbons which comprises contacting said impure acid with hydrogen and at least one hydrogenation catalyst, the improvement comprising said catalyst having a water insoluble and non-brittle coating of at least one polymeric material.

8 Claims, No Drawings

PROCESS FOR THE PURIFICATION OF AROMATIC POLYCARBOXYLIC ACIDS

This is a continuation of application Ser. No. 08/542,229 filed Nov. 6, 1995, which is a continuation of application Ser. No. 08/360,855 filed Dec. 20, 1994 now abandoned.

BACKGROUND OF THE INVENTION

1. Field of the Invention

This invention relates to an improved process for the purification of impure aromatic polycarboxylic acids.

2. Description of Related Art

Processes for the purification of impure aromatic polycarboxylic acids (most notably terephthalic acid) are well known to those of ordinary skill in the art. For example, U.S. Pat. No. 3,584,039 describes that fiber-grade terephthalic acid can be obtained by catalytic hydrogen treatment of solutions of impure terephthalic acid. The treated solution is separated from the catalyst and fiber-grade terephthalic acid is recovered by crystallization and separation from impurities retained in the aqueous mother liquor.

U.S. Pat. No. 3,726,915 describes the alloying of copper with palladium deposited on carbon in the respective weight ratio of less than 0.5:1.0 substantially enhances the catalytic activity of that palladium reduction catalyst especially the selective reduction of formylbenzoic acid impurities in crude phthalic acid products.

U.S. Pat. No. 4,201,872 describes a purified terephthalic acid prepared by dissolving a crude terephthalic acid in water at high temperature under high pressure and then contacting the resulting aqueous solution with a catalyst of an active carbon supporting palladium and maintaining the pressure $P(kg/cm^2)$ of the gaseous phase in the catalytic contacting zone in a range of $Po \leq P \leq Po+5$, wherein Po represents a vapor pressure $(kg/cm^2)$ of the aqueous solution at the reaction temperature, and then cooling the aqueous solution to crystalize terephthalic acid.

U.S. Pat. No. 4,405,809 describes an improved process for purifying aromatic polycarboxylic acid produced by liquid phase catalytic oxidation of polyalkylaromatic hydrocarbon to remove undesirable aldehydearomatic carboxylic acid and other impurities including the step of contacting an aqueous solution of said impure acid and hydrogen with a noble metal-containing catalyst, the improvement comprising eliminating any gas phase during the contacting step and conducting said contacting step with an aqueous solution by maintaining hydrogen at about 10 to about 75% of saturation in the liquid reaction medium to produce purified aromatic polycarboxylic acid having delta Y values below ten.

U.S. Pat. No. 4,791,226 describes a catalyst, a process for preparing said catalyst, and process for producing purified terephthalic acid wherein the 4-carboxybenzaldehyde is reduced to very low levels, wherein said catalyst is produced by contacting a solution of a suitable palladium salt and organic solvent with a suitable activated carbon support, wherein said palladium salt is reduced to palladium metal crystallites by said activated carbon support. Purified terephthalic acid is prepared by hydrogenating crude terephthalic acid in the presence of said catalyst.

U.S. Pat. No. 4,892,972 describes aqueous solutions of crude terephthalic acid purified by hydrogenation in the presence of plural noble metal catalysts in separate layers.

U.S. Pat. No. 5,180,849 describes an improved process for producing purified terephthalic acid which comprises catalytically oxidizing p-xylene in liquid phase to produce crude terephthalic acid containing 4-carboxybenzaldehyde as a main impurity therein, and treating the crude terephthalic acid with hydrogen in the presence of hydrogenation catalyst in a reaction vessel, thereby to produce purified terephthalic acid containing 4-carboxybenzaldehyde in an amount of fixed range in a stationary manner, the improvement comprising feeding into the reactor crude terephthalic acid which contains 4-carboxybenzaldehyde in an amount larger than that in a stationary state of the treatment and treating the terephthalic acid until the treatment reaches the stationary state.

There was still a need, however, for improved processes for the purification of impure aromatic polycarboxylic acids which provide reduced particulate contamination and improved efficiency.

SUMMARY OF THE INVENTION

This invention relates to an improved process for the purification of impure aromatic polycarboxylic acids produced by the catalytic oxidation of polyalkylaromatic hydrocarbons which comprises contacting said impure acid with hydrogen and at least one hydrogenation catalyst, the improvement comprising said catalyst having a water insoluble and non-brittle coating of at least one polymeric material.

DESCRIPTION OF THE PREFERRED EMBODIMENT

As previously stated, this invention provides improvement in processes known to those skilled in the art for purifying impure aromatic polycarboxylic acids. Such acids include terephthalic acid, isophthalic acid, phthalic acid and naphthalene dicarboxylic acid. The patents discussed hereinabove describe processes for the purification of impure aromatic polycarboxylic acids to which the instant invention may be applied and are hereby incorporated herein by reference for their teachings in this regard.

This invention is particularly applicable to the commercially significant process of purifying impure terephthalic acid. The commercial process typically used for preparing terephthalic acid is by the catalytic oxidation of para-xylene. A product of this reaction is described as "crude" terephthalic acid in that it contains a number of by-product impurities which are known to be deleterious to the intended uses of the terephthalic acid. The principle impurity in crude terephthalic acid is 4-carboxybenzaldehyde.

The typical commercial process for purifying impure terephthalic acid comprises contacting the crude terephthalic acid with hydrogen and a hydrogenation catalyst. Hydrogenation is carried out at a temperature of from about 100° C. to about 300° C. and at a pressure of from about 200 up to about 1,500 psig. Purified terephthalic acid (PTA) is recovered by crystallization and separation from the mother liquor which retains the impurities in the aqueous solution.

The commercial embodiment to which the instant invention is applicable usually uses a noble metal-containing catalyst as the hydrogenation catalyst. The typical catalyst being palladium supported on carbon; the preferred carbon support is made from coconut charcoal granules.

The foregoing patents which are incorporated herein by reference are also incorporated for their teachings of purification reaction conditions, supports, catalysts, and methods for their preparation.

The improved process of the instant invention provides increased efficiency through improved catalyst life and activity, and reduced fines produced by the attrition of the catalyst. The improvement provided by the instant invention comprises using a hydrogenation catalyst coated with at least one water insoluble and non-brittle layer of at least one polymeric material.

The catalyst used for the purposes of this invention is for the hydrogenation of the impurities contained in crude aromatic polycarboxylic acids. Typically, these catalysts are group VIII noble metals: ruthenium, rhodium, palladium, osmium, iridium and platinum with platinum and/or palladium being preferred. The typical catalyst being palladium. The hydrogenation catalyst may be supported or unsupported, but is preferably supported by material which is insoluble in water and unreactive with the aromatic polycarboxylic acid being purified at the temperatures and conditions of the purification. Carbons and charcoals are inert and particularly suitable as supports in these reactions. The preferred being those derived from coconut shells. The support may be granular, or formed, e.g. by extrusion, etc. into cylindrical or other shapes; however, typically these supports are granular. These supported catalysts typically contain one or more noble metals in an amount of from about 0.1 up to about 5% and preferably from about 0.3 to about 1% by weight of the supported catalyst; most preferably these catalysts contain 0.5% of noble metal.

The catalysts useful in the instantly claimed process have a water insoluble and non-brittle coating of at least one polymeric material. The polymer coating may be any polymer capable of forming a film which when applied to the surface of the supported catalyst is or can be made to be water insoluble and non-brittle. One or more layers of the same or different polymeric materials are contemplated as being within the scope of this invention.

As used herein the term "water insoluble" shall mean that, under conditions typically used for purification of crude terephthalic acid, the polymer coating is substantially insoluble in water and that water does not materially affect the performance of the catalyst in the instantly claimed process.

The term "non-brittle" as used herein in conjunction with the polymer coatings described herein shall mean that the polymer coating is flexible so as not to easily break or crack or separate from the catalyst particles under conditions of room temperature. Suitable polymeric materials which form the non-brittle polymeric coatings of the instant invention will typically have, when measured in bulk form, an Intrinsic Notched Izod Value (as measured by ASTM D-256-93A) of greater than about 0.15 ft.–lb. per inch; more preferably, will have "no break character" in said Notched Izod Test. This Notched Izod Test is hereby incorporated by reference for its teaching of the procedure for measuring the impact breaking strength (brittleness) of polymer materials.

Polymeric materials suitable for use in the instant invention include one or more of those selected from the group consisting of silicone rubbers, epoxy resins, polyurethanes, polycyanoacrylates, polyacrylates, polymethacrylates, polyolefins and polyesters. These polymers are well known to those of ordinary skill in the art and are commercially available. Preferably the polymers are available as emulsions or latexes dispersed in water. They may also be available in solutions of organic solvents or in solid bulk forms which may be dissolved in a solvent or converted into emulsion or latex form by known methods. Preferably the polymers considered for use in the instantly claimed invention are crosslinkable and thus subject to crosslinking after application to the claimed hydrogenation catalyst. Preferably the crosslinkable polymers are subjected to crosslinking conditions such as exposure to elevated temperature, ultra violet light, peroxides or other chemical and physical conditions appropriate to the types of polymers which result in the water insoluble and non-brittle film properties discussed above and which are well known to those skilled in the art and technology of polymer science.

The polymer may be applied to the supported catalyst by techniques such as physical adsorption from solution, emulsion or suspension or by spraying a solution, emulsion or suspension of the polymer onto the catalyst. Preferably, an aqueous suspension, emulsion or solution of a crosslinkable polymer is sprayed onto the supported catalyst after which the solvent is removed and then the crosslinkable polymer is crosslinked. In one method of applying the polymer, a solution of Dow Corning RTV Silicone Caulk sealant is prepared in hexane solvent by dissolving an amount of polymer sufficient to yield a 1% coating on the catalyst. The total volume of the hexane solution is adjusted to be equal to the pore volume of the dry carbon catalyst to be coated. The solution is sprayed onto the catalyst while it was tumbled and mixed in a rotary spray coater. After the hexane solution is sprayed onto the catalyst, the catalyst is dried at 40° C. for 24 hours in air to remove the hexane and to permit the Dow Corning Silicone to cure, i.e., crosslink and form the desired coating.

In another method of applying the coating, "Super Glue" cyanoacrylate adhesive is dissolved in acetone and sprayed onto the catalyst as described above. After spraying is complete, drying at 40°–50° C. to remove the acetone also caused the Super Glue to cure, i.e. crosslink to form the desired coating. In another method, Dow Corning No. 84 Silicone Rubber emulsion is diluted with sufficient water to equal a volume just slightly greater than the void volume of the catalyst to be coated. Water wet carbon catalyst (approximately 50% moisture) is soaked in this mixture, drained and then dried at 120° C. to form the desired crosslinked silicone rubber coating. The polymer coated catalysts of this invention typically contained from about 0.1% to about 10%, preferably 0.25% up to about 4% by weight of polymer.

This invention is exemplified in the following examples. Of course, these examples are not intended as limiting this invention as modification of the examples by ordinary expedient will be readily apparent to those of ordinary skill in the art.

EXAMPLE 1

Preparation of Cyanoacrylate Polymer on of 0.5% w Pd/4×8 Mesh Carbon Granules

About one liter of 0.5% Pd/4×8 mesh carbon granules, 40–50% moisture, was dried overnight at 120° C. The water adsorption pore volume was determined to be 0.51 cc/g. One hundred fifty grams (150 g.) of this dried Pd/c catalyst was coated with cyanoacrylate polymer by first dissolving in acetone to a total volume of 70 cc. 3 g. of a commercially available cyanocrylate "Super Glue" sold under the brand Duro. This solution was sprayed uniformly onto the catalyst while it was tumbled in a rotary coating device. The coated catalyst was then air dried at 40° C. for 56 hours and then for an additional four hours at 120° C.

EXAMPLE 2

Preparation of Silicone Rubber on 0.5% w Pd/4×8 Mesh Carbon Granules

Another 150 g. portion of the dried Pd/c catalyst prepared in Example 1 was treated with clear silicone rubber sealant commercially available as Dow-Corning RTV.

A coating solution was prepared by dissolving 5 g. of the above-described sealant in hexane to a total volume of 70 cc. The catalyst was uniformly spray coated with the hexane solution of silicone rubber sealant in the same way as in Example 1 above. After coating, the catalyst was air dried at 40° C. for 56 hours, and finally oven dried at 120° C. for 4 hours to insure complete curing and crosslinking of the rubber coating.

EXAMPLE 3

Preparation of Polymer Epoxy on 0.5% w Pd/4×8 Mesh Carbon Granules

A 150 g. portion of the dried Pd/c catalyst prepared in Example 1 was treated with an epoxy polymer glue commercially available under the brand Devcon 2-Ton Epoxy which is a two-part epoxy consisting of a resin and separate hardener.

The coating solution was made up by first dissolving 13.5 g. of the resin in acetone to a total weight of 75 g. Another solution was made by dissolving 14 g. of hardener in acetone to a total weight of 75 g. To make the coating solution, 25 g. of the resin-acetone solution and 25 g. of the hardener-acetone solution were combined and diluted with more acetone to a total weight of 120 g. to make the actual coating solution. After thorough mixing, 49.7 g. of the combined resin plus hardener coating solution was uniformly sprayed onto the catalyst in the same fashion as in Example 1.

After coating, the catalyst was air dried at 40° C. for 56 hours, then oven dried at 120° C. for an additional 4 hours.

The properties before and after coating are shown below.

TABLE I

| | Uncoated 0.5% W Pd/4 × 8 mesh Carbon granules | Coated Catalyst | | |
|---|---|---|---|---|
| | | Example 1 | Example 2 | Example 3 |
| Fines, ppmw | 475 | 460 | about 40 | <10 |
| Attrition, % | 2.2 | 0.9 | about 0.25 | about 0.25 |
| Fresh Rate | 2.3 | 1.63 | 1.73 | 1.75 |
| Aged Rate | 0.92 | 0.73 | 1.4 | 1.07 |

Attrition is measured by ASTM D-4058 Catalyst Attrition Test.

Fines are measured by washing a 25–30 g. portion of the catalyst with a large amount of water, about 2–3 liters, collecting the water and filtering the collected wash water through a Millipore sub-micron filter to recover and weigh the fine particles of carbon which are removed from the catalyst during the washing step.

The fresh rate (activity of fresh catalyst) noted is derived from the measurement of the catalyst's ability to remove 4-carboxyl bezaldehyde impurity in crude terephthalic acid. The rate values shown are in arbitrary units and are on a per gram of catalyst basis. The testing was done in a batch 1 gallon autoclave using PTA purification conditions similar to those disclosed in Example 5 of Pat. No. 4,743,577.

To obtain aged rate (activity of aged catalyst), the fresh catalyst was exposed to PTA purification conditions (as noted above for the fresh rate) for 72 hours before measuring the activity for removing 4-carboxyl benzaldehyde impurity (4-CBA).

EXAMPLE 4

Preparation of Silicone Rubber on 0.5% w Pd/4×8 Mesh Carbon Granules

Approximately 4 liters of wet 0.5% w Pd/4×8 mesh carbon granules (50% by weight moisture, void volume between 1500 and 1600 cc) was thoroughly drained of adhering excess water. A coating solution was prepared by diluting with water 85.7 g. of a silicone rubber emulsion commercially available as Dow-Corning #84 (equivalent to 51.3 g. of silicone rubber solids) to a total volume of 1600 cc and mixing well. This produced a thin, white, milk-like mixture of diluted silicone rubber. The drained but still wet catalyst was slowly poured into the diluted silicone rubber emulsion over a period of about 40 seconds. The coating solution completely covered the catalyst. The catalyst was allowed to stand in contact with the silicone rubber emulsion for 20 minutes to adsorb the rubber. The catalyst plus rubber emulsion was stirred once during the soak period.

After the soak period was completed, the excess liquid coating solution was allowed to drain away from the catalyst. After draining, the catalyst was dried in an air oven at 120° C. for 24 hours to cure and crosslink the silicone rubber coating.

A portion of this catalyst was aged in an operating commercial PTA reactor. The catalyst was contained in a test basket made of 12 mesh titanium screen. Its overall outside dimensions were approximately 3"×10." The basket was divided into two equally sized (3"×3"×5") adjoining compartments by a section of titanium screen fastened in the middle of the basket. The coated catalyst was in one compartment and an uncoated portion of the same catalyst was placed in the adjoining compartment for comparison. In this way, the coated catalyst was compared with a sample of its uncoated precursor knowing that each was subjected to exactly the same sets of conditions.

Properties of both coated and uncoated samples of the catalyst of Example 4 are shown below for before and after commercial aging.

TABLE II

| Feature | Fresh | | Commercially Aged | |
|---|---|---|---|---|
| Measured | uncoated | Coated | uncoated | Coated |
| Pd, wt % | 0.50 | 0.48 | 0.275 | 0.319 |
| Attrition, wt % | 1.15 | 0.33 | 0.55 | 0.20 |
| Fines, ppmw | 460 | 97 | 235 | 24 |
| Surf. Area, m$^2$/g. | 1190 | 1150 | 871 | 883 |
| Lab Aged Rate | 0.907 | 0.974 | — | — |
| Commercial Aged Rate | — | — | 0.157 | 0.228 |

As may be seen clearly from Tables I and II, the advantages of coating include less attrition, lower fines, better retention of activity after aging and for the commercially aged catalyst, less loss of Pd during use in commercial PTA conditions.

What is claimed is:

1. A process for the purification of impure aromatic polycarboxylic acids produced by the catalytic oxidation of polyalkylaromatic hydrocarbons which comprises contacting said impure acid with hydrogen and at least one supported hydrogenation catalyst, wherein said supported catalyst is coated with at least one water insoluble and non-brittle layer of at least one polymeric material.

2. The process according to claim 1 wherein said catalyst is a supported noble metal catalyst.

3. The process according to claim 1 wherein the catalyst is supported on a particulate carbonaceous material.

4. The process according to claim 1 wherein said polymeric material in bulk form has an Intrinsic Notched Izod Value of greater than about 0.15 ft.–lb. per inch.

5. The process according to claim 1 wherein said coating is comprised of a crosslinked polymeric material.

6. The process according to claim 1 wherein the polymeric material is one or more of those selected from the group consisting of silicone rubber, epoxy resins, polyurethanes, polycyanoacrylates, polyacrylates, polymethacrylates, polyolefins and polyesters.

7. The process according to claim 1 wherein said aromatic polycarboxylic acid is selected from the group consisting of terephthalic acid, isophthalic acid, and phthalic acid, and naphthalene dicarboxylic acid.

8. The process according to claim 1 wherein said catalyst is palladium supported on granular coconut carbon charcoal.

* * * * *